US00PP14820P3

(12) United States Plant Patent
Danziger

(10) Patent No.: US PP14,820 P3
(45) Date of Patent: May 25, 2004

(54) IMPATIENS PLANT NAMED 'DANCHELIRED'

(50) Latin Name: *Impatiens walleriana*
Varietal Denomination: Danchelired

(75) Inventor: Gabriel Danziger, Nir-Zvi (IL)

(73) Assignee: Danziger "DAN" Flower Farm (IL)

( * ) Notice: Subject to any disclaimer, the term of this patent is extended or adjusted under 35 U.S.C. 154(b) by 9 days.

(21) Appl. No.: 10/230,305

(22) Filed: Aug. 29, 2002

(65) Prior Publication Data

US 2004/0045067 P1 Mar. 4, 2004

(51) Int. Cl.[7] ..... A01H 5/00

(52) U.S. Cl. ..... Plt./317

(58) Field of Search ..... Plt./317

*Primary Examiner*—Bruce R. Campell

*Assistant Examiner*—June Hwu

(74) *Attorney, Agent, or Firm*—Foely & Lardner

(57) ABSTRACT

A new and distinct Impatiens plant named 'Danchelired' characterized by having compact growth habit; small flowers; small, green leaves; and red flowers.

1 Drawing Sheet

Latin name of the genus and species of the plant claimed: *Impatiens walleriana.*
Variety denomination: Danchelired.

BACKGROUND OF THE INVENTION

The present invention relates to a new and distinct cultivar of Impatiens plant, botanically known as *Impatiens walleriana*, hereinafter referred to by the cultivar name 'Danchelired'.

The new cultivar originated from a cross made in a controlled breeding program in Moshav Mishmar Hashiva, Israel. The female parent is FRA-122 (unpatented, proprietary variety). The male parent is BGA-111 (unpatented, proprietary variety). 'Danchelired' was discovered and selected by the inventor, Gabriel Danziger, as a flowering plant within the progeny of the stated cross in a controlled environment in Moshav Mishmar Hashiva, Israel.

Asexual reproduction of the new cultivar by leaves cutting was first performed in April, 1999 in Moshav Mishmar Hashiva, Israel and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Danchelired' which in combination distinguish this Impatiens as a new and distinct cultivar:

1. compact growth habit;
2. small flowers;
3. small, green leaves; and
4. red flowers.

'Danchelired' has not been observed under all possible environmental conditions. The phenotype of the new cultivar may vary significantly with variations in environment such as temperature, light intensity, and daylength without any change in the genotype of the plant.

Of the many commercial cultivars known to the present inventor, the most similar in comparison to 'Danchelired' is the Impatiens variety 'Fify Red' (U.S. Plant Pat. No. 11,753), commercially known as 'Firefly Red'.

TABLE 1

| | 'Danchelired' | 'Firefly Red' |
|---|---|---|
| Flower Color-upper surface | RHS 46C | RHS 45C |
| Leaf Color-upper surface | RHS 143A | RHS 137C |
| Flower Size | 2.5 cm | 2.5 cm |

BRIEF DESCRIPTION OF THE DRAWING

The accompanying photographic drawings illustrate the overall appearance of the new Impatiens showing the colors as true as is reasonably possible with color reproductions of this type. The drawing shows a whole plant side-view of a flowering potted 'Danchelired' plant.

DETAILED BOTANICAL DESCRIPTION

The following observations, measurements and values describe the new cultivar as grown in Moshav Mishmar Hashiva, Israel under conditions which closely approximate those generally used in commercial practice. The plant was grown in a greenhouse under typical Israeli weather conditions (Winter night time temperature 18° C. winter day time temperature 20–25° C.; summer night time temperature approximately 25° C., summer day time temperature approximately 30° C.). Fertilization: N: P: K=5:3:8, N=100 ppm.

Color references are made to The Royal Horticultural Society Color Chart (R.H.S.), except where general colors of ordinary significance are used. Color values were taken under daylight conditions at approximately 1:00 p.m. In Moshav Mishmar Hashiva, Israel. The age of the plant described is 13 weeks from planting. The plant was asexually reproduced by leaf cuttings.

PLANT

General appearance and form:

*Height.*—12 cm.

*Plant spread.*—Compact, 30 cm.

*Lateral branches.*—Length 11 cm; internode length 2 cm; Diameter 0.5 cm; branch color RHS 143D anthocyanin color RHS 184B.

*Flowering response.*—Flowers at any day length.

*Flowering season.*—Year round as grown in a greenhouse with winter night time temperature of 18° C., winter day time temperature of 20–25° C.; summer night time temperature of approximately 25° C., and summer day time temperature of approximately 30° C.

*Winter hardiness.*—Resistance to 10° C.

*Lastingness of the individual bloom.*—Approximately 15 days.

*Rooting habit description.*—Adventitious roots from cutting base.

*Time to initiate roots.*—10 days.

*Time to produce a rooted cutting or liner.*—17 days.

*Growth and branching habit.*—Compact growth habit; strong branching.

*Crop time.*—Ready for sale 10 weeks after planting in 10–12 cm pot.

*Fragrance.*—None.

Foliage:

*Leaf shape.*—Elliptic.

*Apex.*—Acuminate.

*Base.*—Acute.

*Length.*—Approximately 2.5 cm.

*Width.*—1.5 cm.

*Margin.*—Shallowly serrate.

*Texture.*—Smooth.

*Color of upper surface.*—Mature leaf: RHS 143A. Immature leaf: RHS 146B.

*Color of lower surface.*—Mature leaf: RHS 139C. Immature leaf: RHS 139D.

*Venation.*—None.

*Petiole.*—Length: 1–1.5 cm. Diameter: 1 mm. Color: RHS 145D.

Inflorescence:

*Flower type and habit.*—Single flower, day neutral.

*Overall shape.*—Irregular — 5 petaled.

*Flower size.*—Diameter: Approximately 2.5 cm.

*Average number of flowers per lateral branch.*—5–7.

*Petals.*—Petal Number: 5. Petal Shape: Spatulate; apex obtuse; base acute; margin entire. Texture: Smooth. Petal size: Length 1.5 cm; width 1 cm. Petal Color: Upper surface: RHS 46C. Lower surface: RHS 48A.

*Sepals.*—Number: 2. Shape: Elliptic. Length: 2 mm. Width: 1 mm. Apex: Acute. Margin: Entire. Color: Yellow green, RHS 145C.

*Stem.*—Average length: 11 cm. Average diameter: 0.5 cm. Color: Green RHS 143C. Internode length: 2 cm.

*Spur.*—Length 2 cm; color pink RHS 51D.

*Bud.*—Rate of opening: From the emergence of color until anthesis: 2 days. Color: RHS 159C. Shape: Conical. Length: 0.5 cm. Diameter: 0.3 cm.

*Peduncles.*—Length 1.7 cm; slightly upward angle; stable strength; smooth surface texture; color yellow-green RHS 145B.

Reproductive organs:

*Stamen.*—Size: 2 mm. Number: 5. Color: Purple RHS 77C.

*Seeds.*—Width: 1 mm. Length: 1 mm. Shape: Lanceolate. Color: Brown RHS 165A.

*Fruit.*—Size: 0.5 mm. Color: Green RHS 144A.

*Anthers.*—Color: RHS 63B.

*Pollen.*—None.

*Pistil.*—Size: 2 mm.

*Stigma.*—Color: Green RHS 144B.

*Ovary.*—Color: Green RHS 144D.

Disease resistance: No sensitivity to disease was observed under regular growing conditions.

I claim:

1. A new and distinct Impatiens plant named 'Danchelired', substantially as illustrated and described herein.

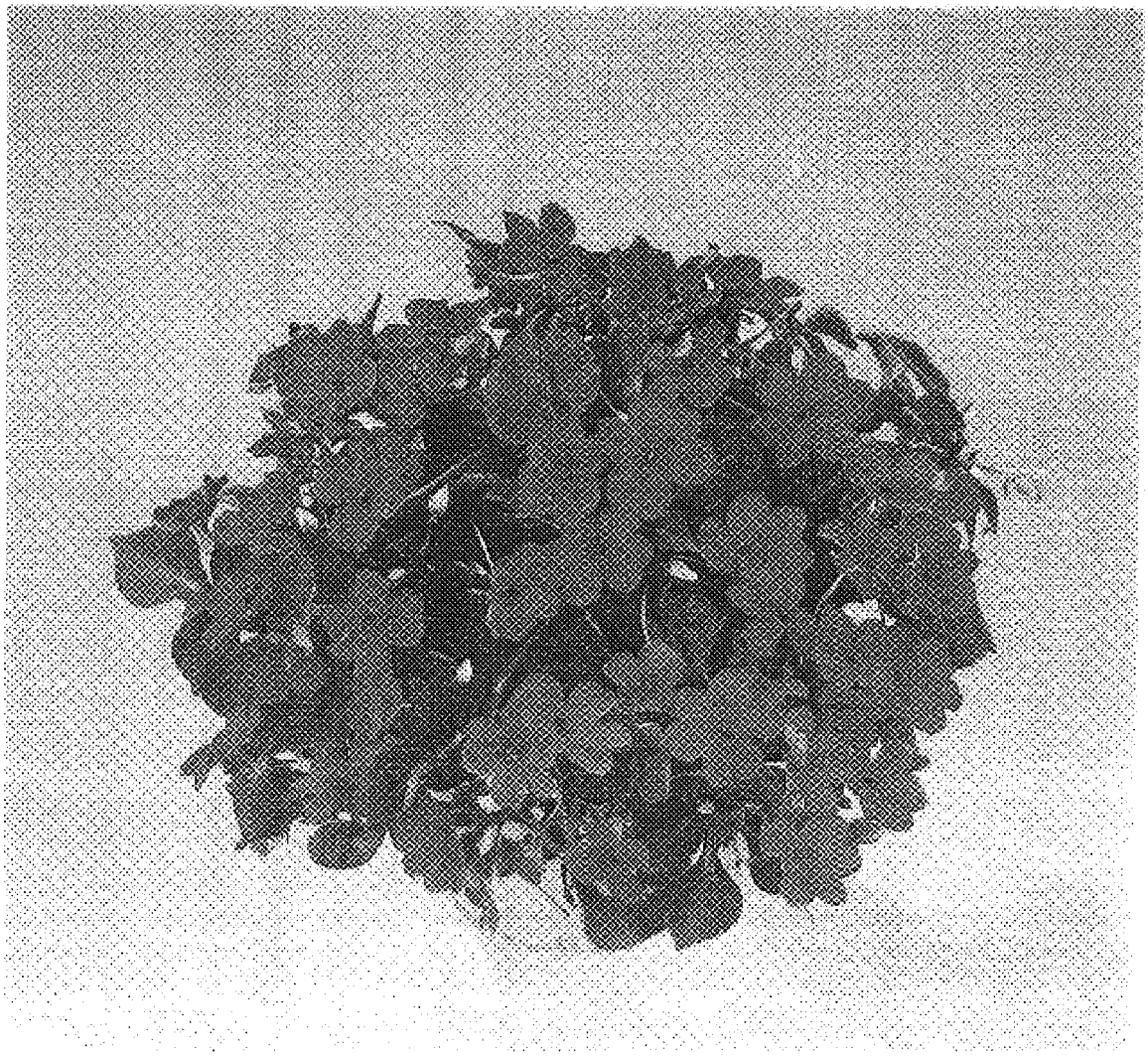

* * * * *